(12) United States Patent
Qiu et al.

(10) Patent No.: US 11,585,785 B2
(45) Date of Patent: Feb. 21, 2023

(54) PORTABLE ODOR QUANTITATIVE DETECTOR

(71) Applicant: HENKEL AG & CO., KGaA, Duesseldorf (DE)

(72) Inventors: Jianlin Qiu, Guangdong (CN); Zhiguo Lu, Guangdong (CN); Yong Chen, Guangdong (CN)

(73) Assignee: HENKEL AG & CO., KGaA, Duesseldorf (DE)

( * ) Notice: Subject to any disclaimer, the term of this patent is extended or adjusted under 35 U.S.C. 154(b) by 134 days.

(21) Appl. No.: 16/205,703

(22) Filed: Nov. 30, 2018

(65) Prior Publication Data

US 2019/0170690 A1  Jun. 6, 2019

Related U.S. Application Data

(63) Continuation of application No. PCT/CN2017/086946, filed on Jun. 2, 2017.

(30) Foreign Application Priority Data

Jun. 2, 2016  (WO) ................ PCT/CN2016/084510

(51) Int. Cl.
| | | |
|---|---|---|
| *G01N 27/626* | (2021.01) | |
| *G01N 1/22* | (2006.01) | |
| *G01N 33/00* | (2006.01) | |
| *G01N 35/10* | (2006.01) | |
| *G01N 1/24* | (2006.01) | |

(52) U.S. Cl.
CPC ......... *G01N 27/626* (2013.01); *G01N 1/2226* (2013.01); *G01N 33/0009* (2013.01); *G01N 35/1079* (2013.01); *G01N 1/24* (2013.01)

(58) Field of Classification Search
CPC ............ G01N 27/626; G01N 35/1079; G01N 33/0009; G01N 1/2226; G01N 1/24
USPC ....................................................... 73/23.34
See application file for complete search history.

(56) References Cited

U.S. PATENT DOCUMENTS

| | | |
|---|---|---|
| 4,369,647 A | 1/1983 | Shigemori et al. |
| 4,823,803 A | 4/1989 | Nakamura |
| 5,014,009 A | 5/1991 | Arimoto et al. |

(Continued)

FOREIGN PATENT DOCUMENTS

| | | |
|---|---|---|
| CN | 2718576 Y | 8/2005 |
| CN | 101587031 A | 11/2009 |

(Continued)

OTHER PUBLICATIONS

Abdullah, et al., "Bacteria Classification Using Electronic Nose for Diabetic Wound Monitoring", Applied Mechanics and Materials, vol. 339 (2013), pp. 167-172.

(Continued)

*Primary Examiner* — Tarun Sinha
(74) *Attorney, Agent, or Firm* — Sun Hee Lehmann

(57) ABSTRACT

The present application discloses a portable odor detector and a method for operating the same, especially for a disposable hygiene product or its raw materials, comprising a housing, a display screen, a battery assembly, a circuit board and a sampling unit, wherein the sampling unit comprises a heat-resistant housing in which a detection chamber is defined, an odor sensor is arranged in the detection chamber.

10 Claims, 8 Drawing Sheets

(56) References Cited

U.S. PATENT DOCUMENTS

| | | | |
|---|---|---|---|
| 6,085,576 A | 7/2000 | Stevens et al. | |
| 6,422,061 B1 | 7/2002 | Sunshine et al. | |
| 6,741,181 B2* | 5/2004 | Skaggs | G08B 17/10 |
| | | | 340/514 |
| 8,752,412 B2 | 6/2014 | Wetzig et al. | |
| 2002/0178789 A1* | 12/2002 | Sunshine | G01N 33/0009 |
| | | | 73/31.06 |
| 2009/0142233 A1* | 6/2009 | Antieau | G01N 33/0009 |
| | | | 422/83 |
| 2011/0234235 A1 | 9/2011 | Guan et al. | |
| 2014/0260543 A1 | 9/2014 | Zielinski et al. | |
| 2014/0326042 A1* | 11/2014 | Zhou | G01N 1/24 |
| | | | 73/23.3 |
| 2015/0101392 A1 | 4/2015 | Foote | |
| 2015/0253165 A1* | 9/2015 | Ajay | G08B 17/10 |
| | | | 73/28.01 |

FOREIGN PATENT DOCUMENTS

| | | |
|---|---|---|
| CN | 201955325 U | 8/2011 |
| CN | 202141606 U | 2/2012 |
| CN | 102495161 A | 6/2012 |
| CN | 202330379 U | 7/2012 |
| CN | 104316112 A | 1/2015 |
| JP | H01212349 A | 8/1989 |
| JP | H06308069 A | 11/1994 |
| JP | H08266983 A | 10/1996 |
| JP | 2010539461 A | 12/2010 |
| KR | 20010042081 A | 5/2001 |
| WO | 2013108071 A2 | 7/2013 |

OTHER PUBLICATIONS

Baldwin, et al., "Electronic Noses and Tongues: Applications for the Food and Pharmaceutical Industries", Sensor 2011, May 2, 2011, pp. 4744-4766.

Rasulev, et al., "Surface-ionization methods and devices of indication and identification of nitrogen-containing base molecules", Journal of Chromatography A., vol. 896, 2000, pp. 3-18.

Great Soviet Encyclopedia, ch. ed. Prokhorov A.M., Moscow, Soviet Encyclopedia, 1972, third edition, vol. 9, p. 349, col. 1035.

The Biological Encyclopedic Dictionary, ch. ed. Gilyarov M.S., Moscow, Soviet Encyclopedia, 1986, p. 415, column 3, line 28-p. 416, column 2, line 5.

Physiology of sensory systems and higher nervous activity, ed. Altman Ya. A. et al., Moscow, Academy, 2009, vol. 1, p. 188, line 13-p. 190, line 8.

\* cited by examiner

PORTABLE ODOR QUANTITATIVE DETECTOR

FIELD OF THE INVENTION

The present application generally relates to a portable odor quantitative detector, especially a detector which is used to carry out odor quantitative detection for a disposable hygiene product or its raw materials.

BACKGROUND OF THE INVENTION

For the sake of environmental protection and personal health, odor requirements for industrial products (such as automobile interiors, home textiles, especially disposable hygiene products or their raw materials and the like) become strict. Take the disposable hygiene products as examples, adhesives are used for their production and thus odor requirements for them are extremely strict in order to satisfy customers.

Now, a commonly-used odor detection method is to carry out an artificial grouping test. For instance, test persons are divided into several groups. Each group of test persons smell, by their respective noses, a disposable hygiene product to be tested and then score in a prescribed table. Finally, score results of each group are averaged to determine respective odor values. However, this group testing method is inadequate in that everyone's olfaction is different, and thus an odor of the same concentration might be scored very differently by test persons such that it is hard to evaluate the odor in an objective and quantitative manner. Furthermore, even if the disposable hygiene product to be tested is smelt in a closed chamber, the odor will diffuse in air. The odor may diffuse at different speeds depending on types of samples to be tested. Such difference between the different diffusing speeds may affect smelling results of the test persons.

A Gas Chromatography-Mass Spectrometer (GC-MS) can also be used for odor detection. Although such a spectrometer can be used to detect the odor of a sample in a precise and quantitative manner, it is huge and thus is suitable for use in laboratories only. Further, because each test should be accomplished by the spectrometer for a longer time, the spectrometer cannot be widely used in production. Meanwhile, the spectrometer is expensive, and its use and maintenance costs are high. This results in that the spectrometer cannot be widely used in production and operation activities.

Furthermore, sometimes, it is necessary to make odor detection for a packaged disposable hygiene product so as to determine whether the product meets regulatory requirements. Usually, the product's package need be opened, and the disposable hygiene product is taken off to be tested. After being inspected, the disposable hygiene product must be repackaged, which takes time and efforts. If the odor detection is made for more packages, relevant packaging and transporting costs increase greatly.

SUMMARY OF THE INVENTION

In order to solve those problems mentioned previously, the present application aims at proposing an odor quantitative detector by which odor of a product, for example a disposable hygiene product or its raw materials can be detected in a relatively objective and quantitative manner. The proposed odor quantitative detector should be small and is suitable for use in production and operation activities. Further, odor detection can be made using the proposed odor quantitative detector in the case of the product's package being unbroken, which can keep detecting costs down.

The present application proposes a portable odor detector, especially for a disposable hygiene product or its raw materials, comprising a housing, a display screen, a battery assembly, a circuit board and a sampling unit, the circuit board being electrically connected to the display screen, the battery assembly and the sampling unit, and the battery assembly and the sampling unit being held within the housing, wherein the sampling unit comprises a heat-resistant housing in which a detection chamber is defined, an odor sensor is arranged in the detection chamber, the sampling unit comprises an air pump having a suction port in airtight communication with the detection chamber, wherein an airflow sampling passage and an airflow returning passage are defined in the heat-resistant housing such that the two passages are in airtight communication with the detection chamber, by operating the air pump, a test airflow from an object to be tested can be sucked into the detection chamber through the airflow sampling passage and then discharged out through the airflow returning passage, and the odor sensor can heat the airflow in the detection chamber so as to decompose gas molecules of the test airflow into charged ions which can be converted to electrical signals, which signals can be transmitted to the circuit board for storage and/or displayed on the display screen as test results.

Optionally, the portable odor detector comprises a piercing unit, the piercing unit includes a sampling needle tube and a returning needle tube, each needle tube is hollow and has a free end which is sharp and closed, the sampling needle tube has an internal passage in airtight communication with the airflow sampling passage, the returning needle tube has an internal passage in airtight communication with the airflow returning passage, and each needle tube is provided with a radial aperture adjacent the sharp free end, which radial aperture is in communication with the internal passage.

Optionally, the sampling needle tube is longer than the returning needle tube.

Optionally, the odor sensor has a sensor resolution in the range of 2 to 8 µg/L and an operating temperature in the range of 300° C. to 400° C., preferably 320° C.

Optionally, the heat-resistant housing of the sampling unit is made of aluminum alloy.

Optionally, the battery assembly comprises a rechargeable battery.

Optionally, the display screen is a touch screen which can be used to control the sampling unit.

Optionally, the airflow sampling passage is substantially parallel to the airflow returning passage, and the sampling needle tube is substantially parallel to the returning needle tube.

The present application also proposes a method for operating said portable odor detector, comprising:

powering on the portable odor detector and activating its odor sensor only;

activating an air pump of the portable odor detector only after a first standby time;

connecting an airflow sampling passage of the portable odor detector to a object to be tested, only after a second standby time, to carry out odor detection.

Optionally, during the odor detection, prior to each odor test, separating the portable odor detector from the object to be tested, activating the air pump of the portable odor detector and waiting for the second standby time.

Optionally, the first standby time is greater than the second standby time.

Other individual features or features which are combined with other features so as to be considered as belonging to the characteristic of the present invention will be described in the attached claims.

The configuration of the present invention and other objectives and beneficial effects thereof will be well understood by description of preferred embodiment in accompany of the drawings.

BRIEF DESCRIPTION OF THE DRAWINGS

As a part of the description and in order to provide further explanation of the present invent, the drawings illustrate preferred embodiments of the present invention, and together with the description are used to explain the principle of the present invention. In the drawings.

DETAILED DESCRIPTION OF PREFERRED EMBODIMENTS

Figure 1:
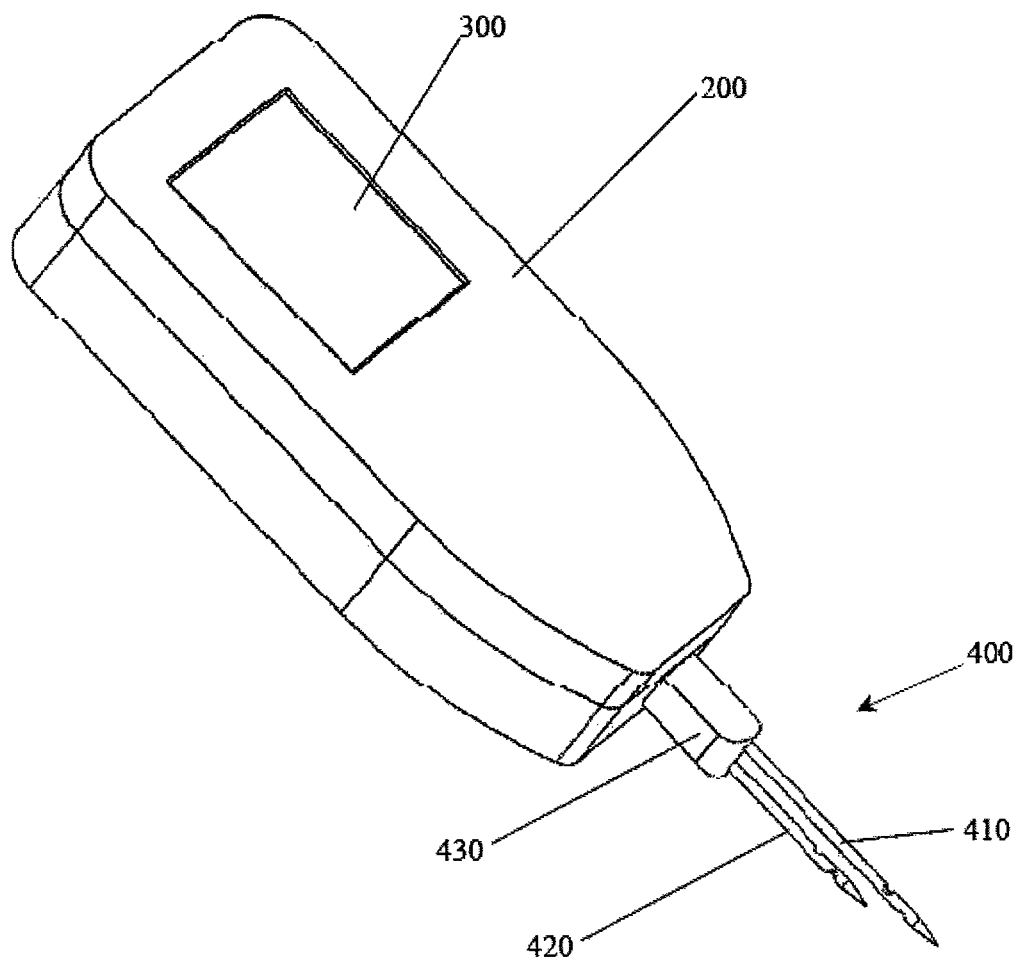
FIG. 1 is a perspective view schematically illustrating a portable odor detector according to one embodiment of the present application.

In the drawings of the present application, features having the same configuration or function are represented by the same reference numerals. Although those drawings are prepared in different scales, this cannot be deemed giving any limitation to the present application.

FIG. 1 schematically illustrates a portable odor (intensity) detector 100 according to one embodiment of the present application. The portable odor detector 100 comprises a housing 200, a touch screen 300 which is exposed in one side of the housing 200, and a piercing unit 400. The housing 200 is sized such that it can be handheld.

Figure 2:
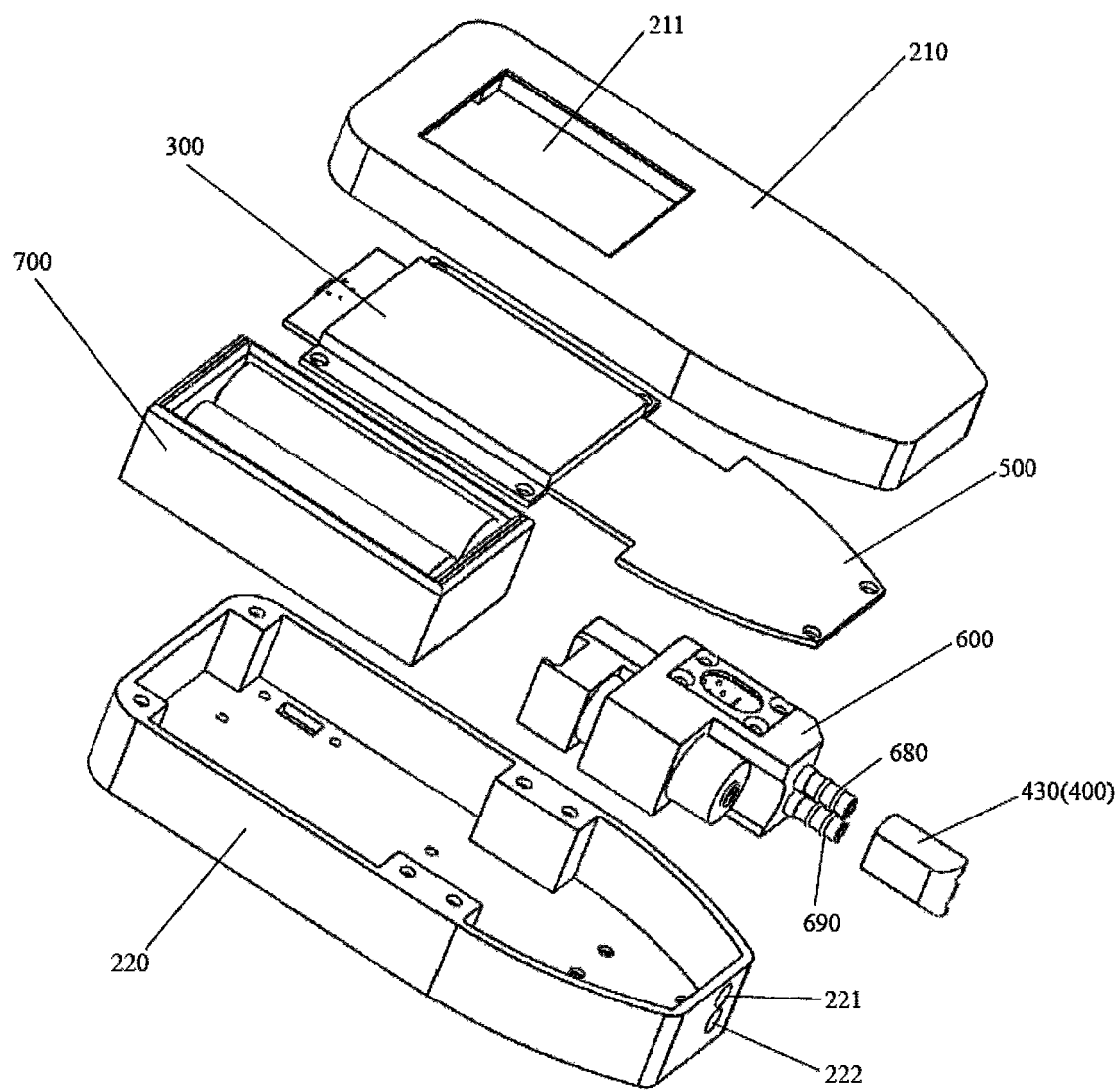
FIG. 2 is an exploded and perspective view schematically illustrating the portable odor detector of FIG. 1.

The housing 200 can be for example made of plastics or any other strong and lightweight materials. Further as shown in FIG. 2, the housing 200 comprises a first housing section 210 and a second housing section 220. The two housing sections can be provided with matable snapping structures on their edges respectively, such that the sections can be snapped together to define a cavity therebetween. Received in the cavity are the touch screen 300, a circuit board 500, a sampling unit 600 and a battery assembly 700. They can be fixed in place relative to the housing 200 by passing screws through them and fitting the screws in threaded holes of the housing 200, especially the second housing section 220.

For example, an opening 211 is formed in the first housing section 210. After the housing 200 is assembled, the touch screen 300 is exposed through the opening such that an operator can view and operate the screen. The touch screen 300 can be a touch screen used in a small handheld device for example a cell phone. The circuit board 500 can be electrically connected to the touch screen 300 and the sampling unit 600, such that the touch screen 300 can be used to control the sampling unit 600. To this end, the circuit board 500 is provided with a dedicated control chip thereon.

The battery assembly 700 is used to supply electric energy to the touch screen 300, the circuit board 500 and the sampling unit 600. As shown in FIG. 2, the battery assembly 700 comprises two 18650-type batteries. In case that the battery is a rechargeable battery, the circuit board 500 can be provided with a relevant charging circuit therein such that when the portable odor detector 100 is connected to an external power source, the battery can be recharged. Furthermore, the battery of the battery assembly 700 can be removable. For example, a removable cover can be provided in a side of the second housing section 200 such that the old battery can be replaced with a new one by removing the cover.

Furthermore, an ON/OFF button 1000 (see FIG. 6) can be provided at a side of the housing 200, which button is connected to the circuit board 500 so as to switch the portable odor detector 100 on or off.

The piercing unit 400 is located outside the housing 200. The piecing unit 400 comprises two needle tubes 410 and 420 as well as a connector housing 430. For instance, the needle tube can be made of metal and is hollow. Each needle tube has a free end which is sharp and closed and thus can be used to pierce into an object. Further, a wall part of each needle tube adjacent the sharp end is formed with at least one radial aperture (two radial apertures being shown). For example, the radial apertures of the two needle tubes 410 and 420 are oriented along different directions such that airflow from an object to be tested can be absorbed in different directions and can be re-circulated.

The connector housing 430 of the piercing unit 400 can be for example made of plastics or any other suitable materials, and has two penetrative connecting passages. Ends of the two needle tubes 410 and 420 opposite to the sharp end are secured in the penetrative connecting passages respectively. For example, the securing can be carried out by bonding or any other suitable manner, such that an internal hollow passage of each needle tube can be in communication with a relevant connecting passage.

The sampling unit 600 is equipped with two connectors 680 and 690. The two connectors 680 and 690 can at least partially pass through two openings 221 and 222 of the housing 200 respectively. In this way, after the housing 200 of the portable odor detector 100 is assembled, the two connectors 680 and 690 can be exposed outwards. The two connectors 680 and 690 can be inserted into the two penetrative connecting passages of the connector housing 430 from a side opposite to the needle tubes 410 and 420 such that the connectors can be in communication with the internal hollow passages of the needle tubes respectively. In order to ensure good air tightness, a sealing ring can be sleeved onto each of the connectors 680 and 690 before they are inserted into the respective connecting passages. In order to prevent the connectors from unexpectedly falling off when the piercing unit 400 in use is pulled out from the object to be tested, the connectors 680 and 690 should be inserted in the respective connecting passages in an interference fit manner. In order that the piercing unit 400 can be replaced after long-term use, it can be configured such that the piercing unit 600 can be pulled out from the connectors by exerting a great pulling force thereon. Preferably or alternatively, they can be bonded together in an airtight manner by adhesives.

Figure 3:
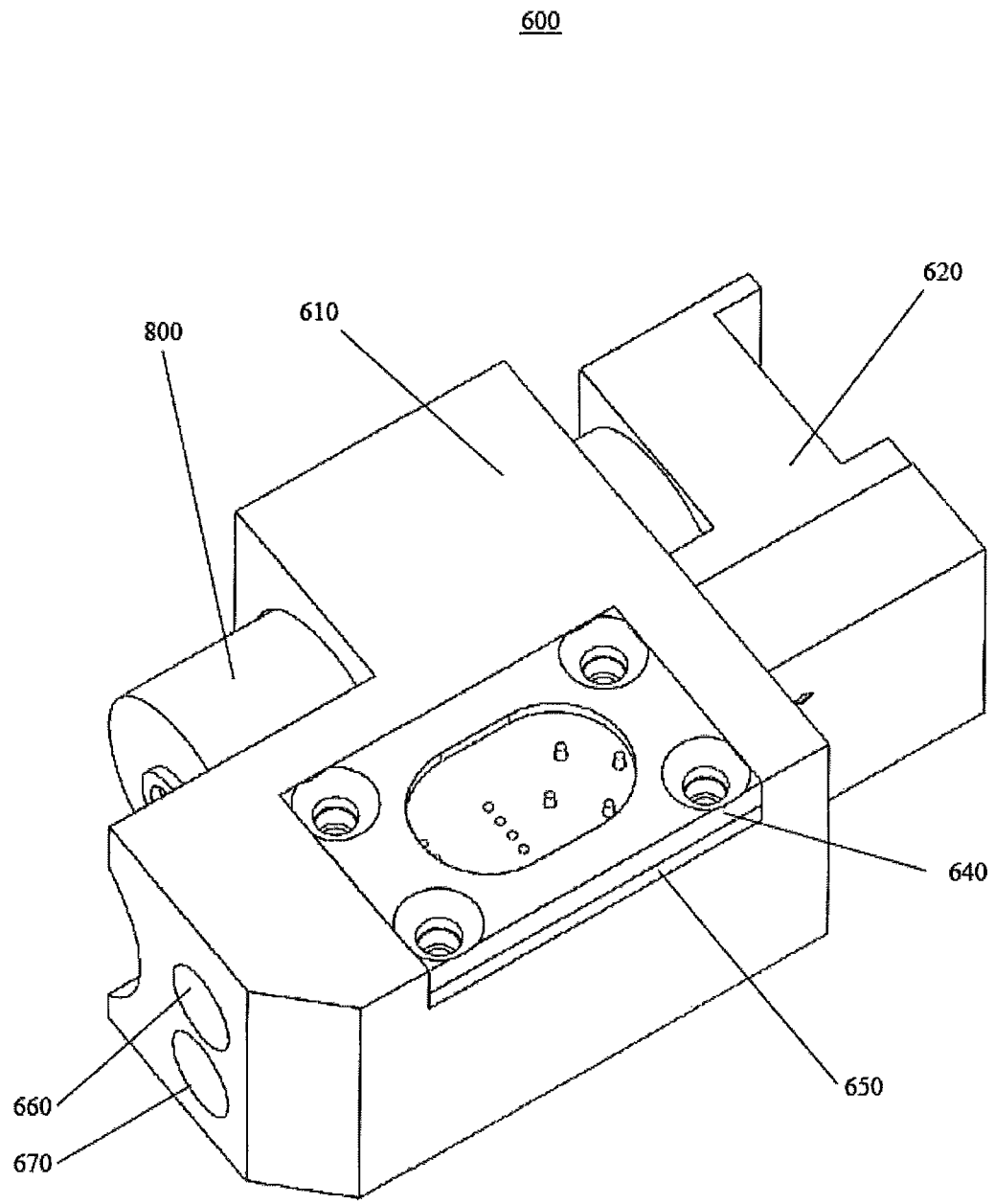
FIG. 3 is a perspective view schematically illustrating one example of a sampling unit of the portable odor detector.

Now, the concrete structure of the sampling unit 600 will be explained with regard to FIGS. 3 to 5 below.

The sampling unit 600 comprises a housing 610 which can be made of aluminum alloy. It is appreciated by a person skilled in the art that any suitable strong, lightweight and heat-resistant material can be used to make the housing 610. A detection chamber 630 is formed in the interior of the housing 610. The sampling unit 600 further comprises a sensor installing plate 650. An odor sensor 651 and its control chip are installed on the sensor installing plate 650. For example, the odor sensor 651 can be designed such that its sensor resolution is in the range of 2 to 8 μg/L and its operating temperature is in the range of 300° C. to 400° C. An opening is formed in a side of the housing 610 so as to be in communication with the detection chamber 630. This opening can be covered by the sensor installing plate 650.

It is appreciated that the odor sensor 651 should be located at a side of the sensor installing plate 650 facing the opening, such that after the opening is covered by the sensor installing plate 650, the odor sensor 651 can be within the detection chamber 630. A sensor installing cover 640 is attached on the sensor installing plate 650. The sensor installing cover 640 is formed with an opening 641. Several holes are formed in the housing 610, the sensor installing cover 640 and the sensor installing plate 650. As shown in FIG. 3, after the sensor installing cover 640 together with the sensor installing plate 650 is fixed in placed by fitting screws in the holes, contacts at a side of the sensor installing plate 650 opposite to the detection chamber 630 are exposed through the opening 641 such that the contacts can be connected to contacts on the circuit board 500.

Figure 4:
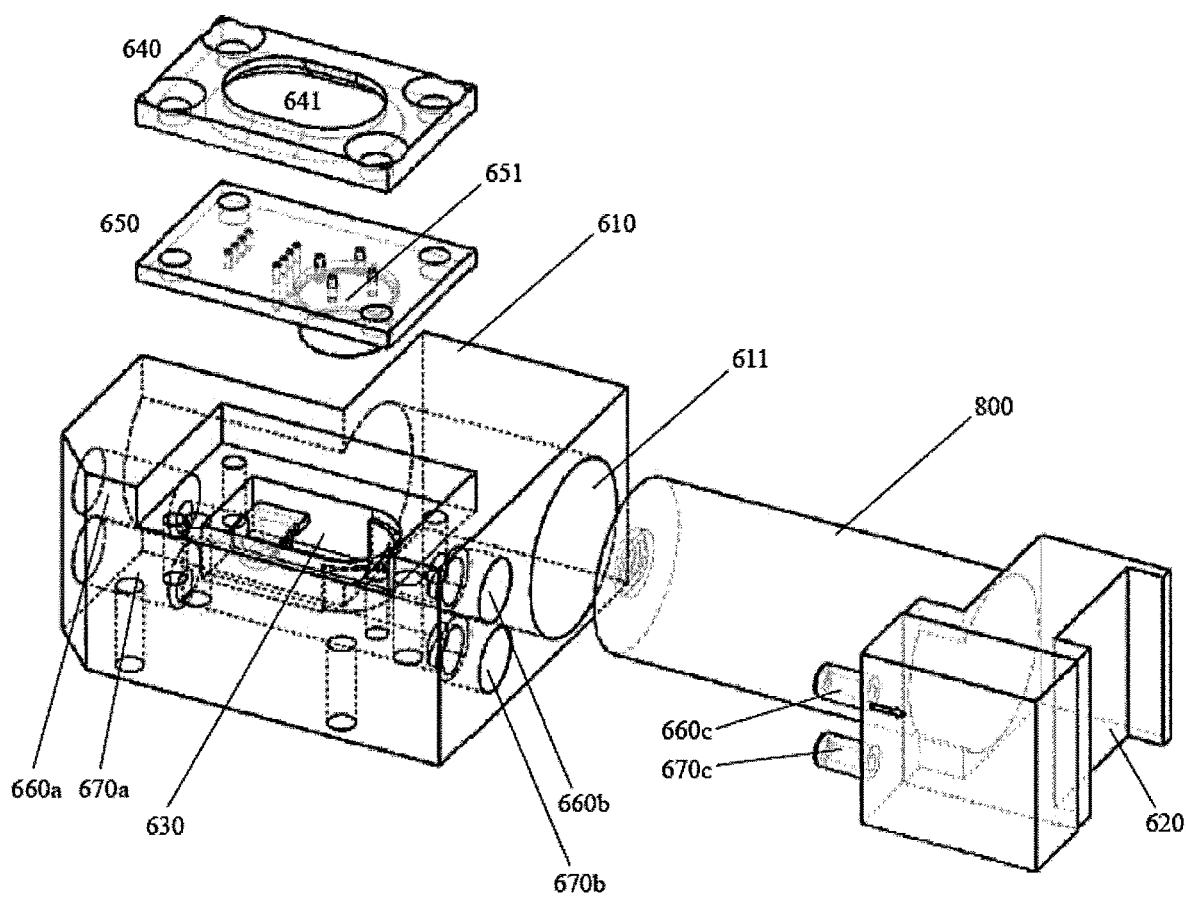
FIG. 4 is an exploded and perspective view schematically illustrating the sampling unit of FIG. 3.
Figure 5:
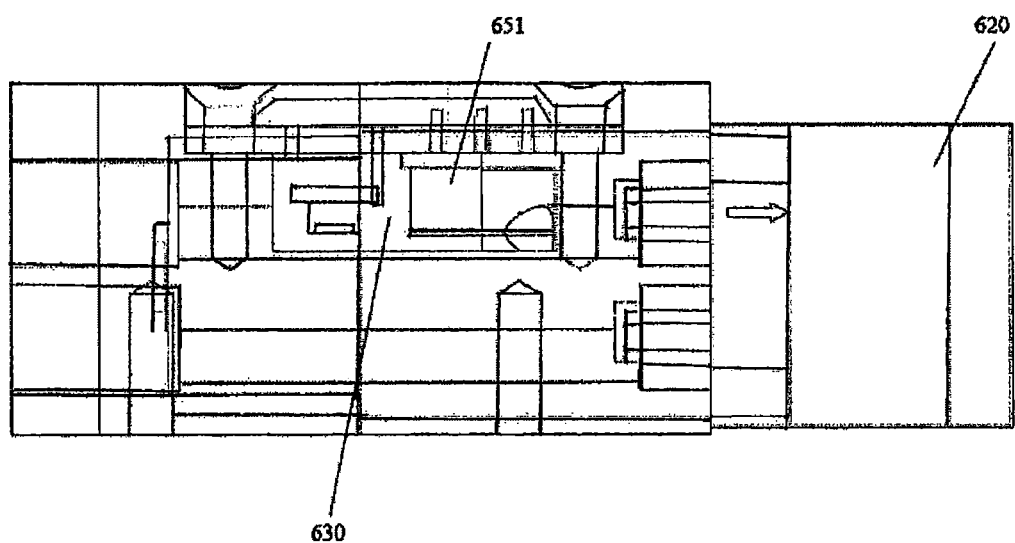
FIG. 5 is a cross-sectional view schematically illustrating the sampling unit of FIG. 3.

As shown in FIG. 4, a pair of through holes 660a, 670a and a pair of through holes 660b, 670b are formed in two sides of the housing 610 respectively. These through holes 660a, 670a, 660b and 670b are in communication with the detection chamber 630.

The sampling unit 600 further comprises an air pump 800. At least a part of the air pump 800 passes through a through hole 611 of the housing 610 such that it is supported therein. It should be understood that this through hole 611 is isolated from the detection chamber 630. As shown, an additional pump base 620 is coupled to the air pump 800. This pump base 620 can be made of plastics or the same material as the housing 610. The pump base is provided with an internal passage which is hermetically connected to a suction port of the air pump 800. Two connectors are secured on a side of the pump base 620. The two connectors are respectively formed with passages 660c and 670c therein, which passages can be in communication with the suction port of the air pump 800 via said internal passage. The two connectors can be hermetically inserted in the passages 670b and 670b respectively such that the passages 660a, 660b and 660c constitute an airflow sampling passage 660, and the passages 670a, 670b and 670c constitute an airflow returning passage 670. Preferably, the airflow sampling passage 660 is parallel to the airflow returning passage 670. Further, the two needle tubes 410 and 420 can also be parallel substantially to each other.

In assembling the sampling unit 600, the connectors 680 and 690 are hermetically inserted into the passages 660a and 670a respectively such that the connectors 680 and 690 can be in communication with the airflow sampling passage 660 and the airflow returning passage 670 respectively.

In the embodiment of the present application, the needle tube 410 of the piercing unit 400 can be called as a sampling needle tube and the needle tube 420 of the piercing unit 400 can be called as a returning needle tube. In this way, after the piercing unit 400 is mounted in place, the internal hollow passages of the needle tubes 410 and 420 can be in airtight communication with the airflow sampling passage 660 and the airflow returning passage 670 via the connectors 680 and 690 respectively.

In the embodiment of the present application, the detection chamber 630 can be formed such that it is small in volume and can just receive the odor sensor 651. In this way, odor detection can be carried out in a relatively small and confined space such that the any difference of test result caused by odors diffusing speeds of different samples can be avoided, and thus the reliability and repeatability of the portable odor detector according to the present application can be enhanced.

Further, according to the present application, an object can be expediently pierced by the needle tube of the piercing unit, such that a packaged object can be tested with minimum damage to the object's package. In this way, the problem in the prior art, in which repackaging the tested object leads to increased testing costs, can be solved.

Further, as shown in FIG. 1, according to the present application, the sampling needle tube 410 is provided longer than the returning needle tube 420. Further, the portable odor detector 100 of the present application is not limited to detect the packaged object. Rather, the needle tube of the portable odor detector can be expediently inserted into a container (bottle) to be tested, such that odor in its interior can be detected. That is to say, the portable odor detector covers a great range of applications.

Now, the operating principle of the portable odor detector 100 according to the embodiment of the present application will be explained with regard to FIG. 6 below.

After the air pump 800 is powered on, airflow from an object to be tested is sucked by the sampling needle tube 410 through the sampling passage 660 into the detection chamber 630. The sucked airflow flows through a surface of the odor sensor 630 in the detection chamber 630. Odor detection quantity can be converted into electrical signals by operation of the odor sensor 630. Then, the airflow is discharged out of the detector through the returning passage 670 and the returning needle tube 420. The electrical signals are treated or stored by the circuit board 500, and can be displayed in real time on the touch screen 300 so as to be observed by the operator. Because of air tightness between the sampling passage and the sampling needle tube and between the returning passage and the returning needle tube, throughout the detection process, the total amount of gas does not decrease, which results from returning of the airflow of the object to be tested. Therefore, the sampled airflow is stable and thus the gas concentration and pressure within the detection chamber 630 can substantially keep constant, such that a reliable and repeatable final detection result can be ensured.

For odor detection of a disposable hygiene product or its raw materials, in order to obtain the electrical signals, the odor sensor 630 should heat the airflow through it to a temperature of 320° C., enabling gas molecules of the airflow to be decomposed into charged ions. Then, the odor can be quantified in odor value as a function of the electrical conductivity of the charged ions, such that quantitative electrical signals can be generated correspondingly. Preferably, the odor sensor 630 can work at an environmental temperature in the range of −40° C. to 120° C. and at an environmental humidity in the range of 5% to 95%. The sensor has a zeroing time of about 60 seconds. Power consumption is only 41 mW in order to heat the odor sensor to the operating temperature of 320° C., and power is saved.

Figure 7:
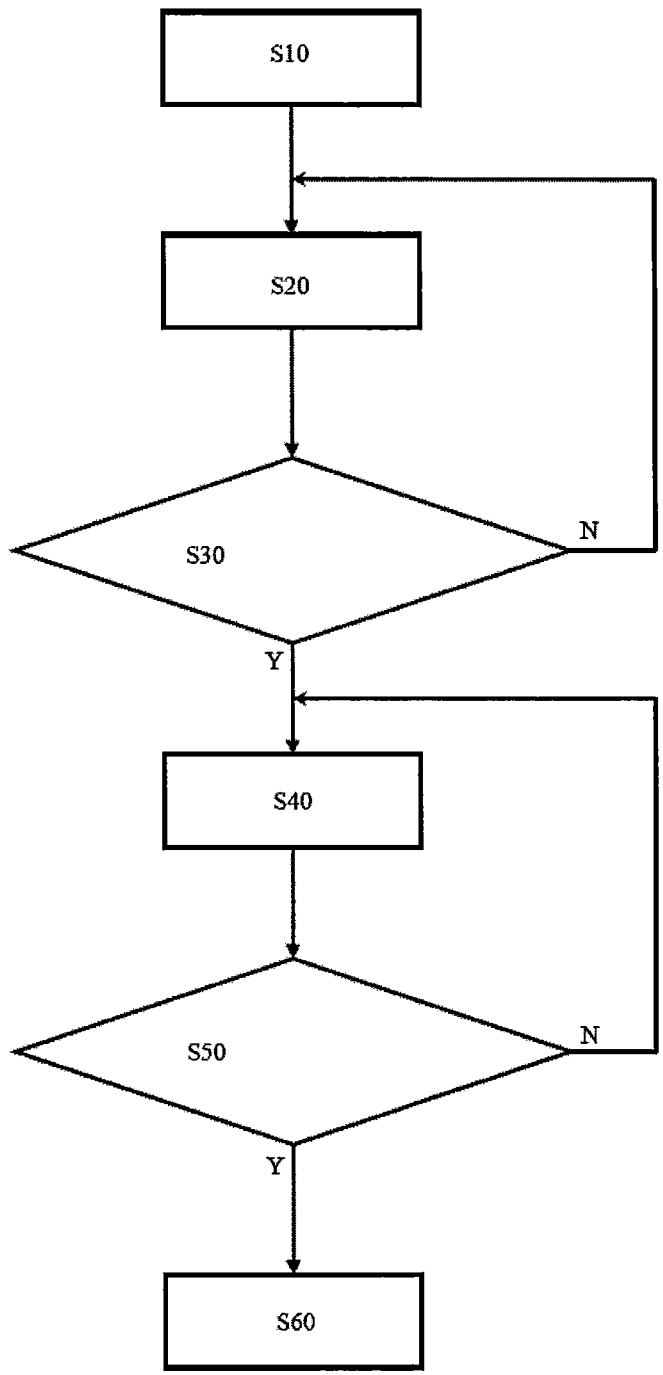
FIG. 7 illustrates a flow chart of one example of a method for operating the portable odor detector according to the embodiment of the present application.

FIG. 7 illustrates a method according to one embodiment of the present application for operating the portable odor detector 100.

At step S10, the ON/OFF button 1000 is depressed to power the odor detector 100 on. Now, all electric components connected to the battery assembly 700 are powered on.

At step S20, the odor sensor 651 is powered on but is in a standby state in order to allow it working stably.

At step S30, it is judged whether the standby state has lasted for a first standby time (for example 30 minutes). If the judgment result is NO, the method goes to the step S20. If the judgment result is YES, the method goes to step S40.

At the step S40, the air pump 800 should be activated, for example via the touch screen 300 by the operator. However, in order to ensure that the internal environment of the detection chamber 630 is stable, the air pump 800 is operated but the needle tube should not be inserted into the object to be tested until detectable values of the odor sensor 651 becomes stable.

At step S50, it is judged whether the waiting has lasted for a second standby time (for example 5 minutes). If the judgment result is NO, the method goes to the step S40 and continues to wait. If the judgment result is YES, the method goes to step S60.

Figure 6:
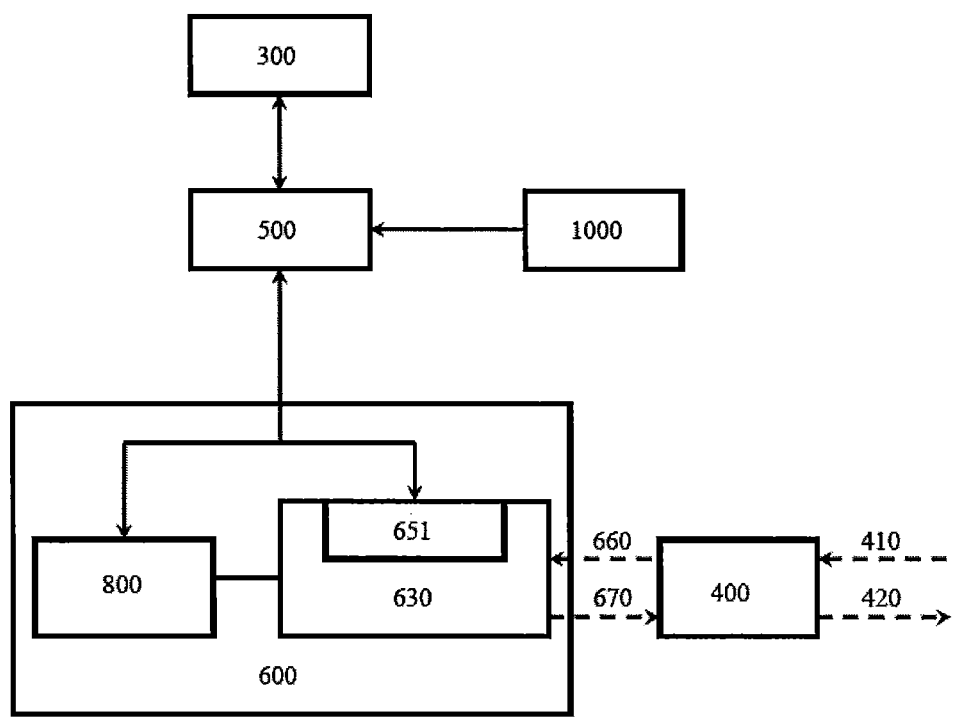
FIG. 6 illustrates a systematic chart of the portable odor detector according to the embodiment of the present application.

At the step S60, the object can be detected by the portable odor detector 100 of the present application in a manner illustrated by FIG. 6.

It should be understood that throughout the odor detection process, only the steps S40 and S50 can be carried out prior to each odor test.

The waiting in the steps S20 and S40 and the judging in the steps S30 and S50 can be visually displayed on the touch screen 300. Further, if necessary, the first and second standby times can be reset on the touch screen 300. Furthermore, at the step S60, in a prescribed period (for example 35 seconds), the odor test can be constantly circled and the odor values are displayed on the touch screen 300. After the prescribed period, the maximum and/or average value among the odor values can be displayed on the touch screen 300 as a final result.

The skilled person in the art should understand that after the detection is accomplished and the needle tube is pulled out from the object, the air pump can be operated for a period before powering it off, such that any odor residue in the detection chamber can be emptied and the detection chamber can be ready for next detection.

Figure 8:
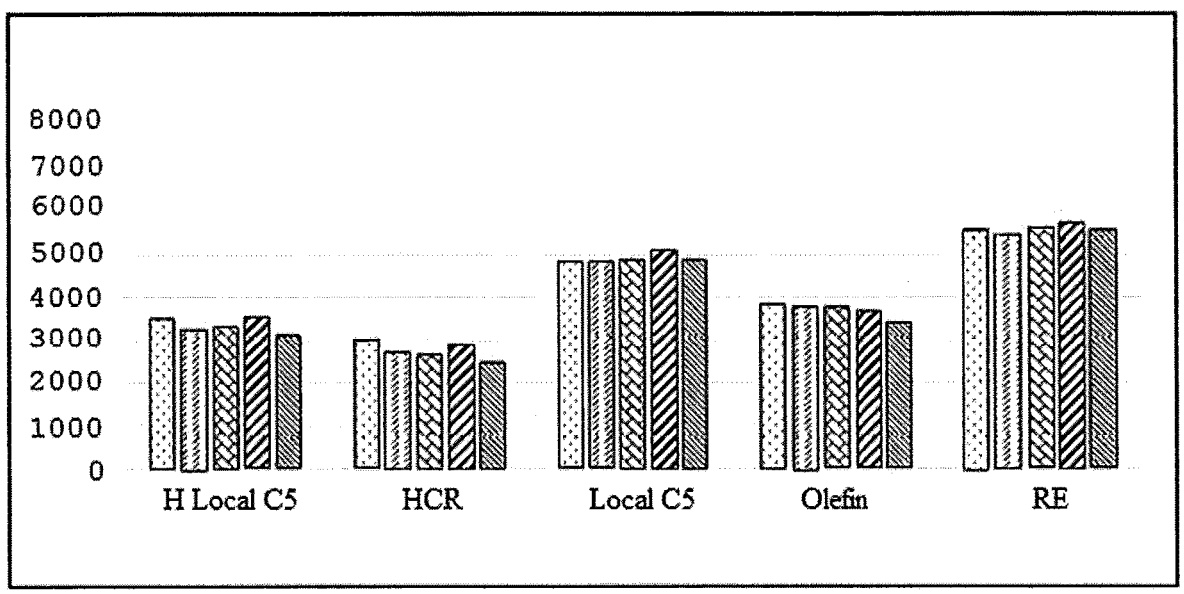
FIG. 8 is a view illustrating results of a test in which five disposable hygiene products are detected by the portable odor detector according to the present application.

FIG. 8 schematically illustrates results of an experiment in which five disposable hygiene products are detected in term of their odor by the portable odor detector 100 according to the present application, and the five disposable hygiene products are treated with five adhesives of the applicant respectively. The five adhesives are Local hydrocarbon petroleum resin adhesive (H Local C5), Import hydrocarbon petroleum resin adhesive (HCR), Local non-hydrocarbon petroleum resin adhesive (Local C5), Olefin adhesive (Olefin) and Rosin ester resin adhesive (RE). In five days of the experiment, samples of each disposable hygiene product are measured once a day. In FIG. 8, first day measured result is illustrated in small dots; second day measured result is illustrated in dashes; third day measured result is illustrated in brick; fourth day measured result is illustrated in ascending stripes; and fifth day measured result is illustrated in thin descending stripes. It can be seen in FIG. 8 that measured results for each disposable hygiene product in five days are relatively average, which means that the repeatability of the portable odor detector is adequate. Therefore, the portable odor detector of the present application can be used to carry out quantitative odor detection for the disposable hygiene product or its raw materials.

Using the portable odor detector of the present application, the object to be tested, especially the disposable hygiene product or its raw materials can be detected quickly and flexibly. Furthermore, the portable odor detector is especially adapted to carry out quantitative odor detection for the disposable hygiene product so as to avoid the technical problem existing in the prior art that no quantitative odor detection can be carried out for the sake of individual differences of the group test. Meanwhile, according to the portable odor detector explained here, because the detection chamber is hermetic and small, the difference of test results caused by odor diffusing speeds of different samples can be avoided. Furthermore, using the portable odor detector of the present application, the odor of the disposable hygiene product or its raw materials can be detected without substantially damaging the original package, and thus relevant detecting costs can be kept down.

Although some embodiments of the present application have been described here, it should be understood by the skilled person in the art that the present application is not limited to those described. In an alternative embodiment, the housing 610 of the sampling unit 600 can be integrally formed with the pump base 620. In order to improve the air tightness of the detection chamber 630, a sealing gasket can be clamped between the sensor installing plate 650 and the housing 610. In an alternative embodiment, the piercing unit 400 can be coupled to the sampling unit 600 by two hose tubes, which can improve the detector's application flexibility. If the object can be detected without damaging its package, even the piercing unit 400 can be dispensed with. Further, the skilled person in the art should appreciate that the touch screen 300 can be replaced with a conventional display screen for showing detecting results only. In this case, an additional depressible key can be provided in the housing 200 to achieve relevant controlling function.

Although several embodiments according to the present application have already been explained, they are given as examples only and cannot be considered to make any limitation to the scope of the present application. The embodiments can be carried out in other suitable manners, and their alternations, changes or modifications can be made without departing from the spirit of the present application. Those embodiments and their modifications should be deemed as being included in the scope and content of the present application, and included in the application recorded by appended claims and theirs equivalents.

The invention claimed is:

1. A portable odor detector, especially for a disposable hygiene product or its raw materials, comprising a housing, a display screen, a battery assembly, a circuit board and a sampling unit, the circuit board being electrically connected to the display screen, the battery assembly and the sampling unit, and the battery assembly and the sampling unit being held within the housing, wherein the sampling unit comprises a heat-resistant housing in which a detection chamber is defined, an odor sensor is arranged in the detection chamber, the sampling unit comprises an air pump having a suction port in airtight communication with the detection chamber, wherein an airflow sampling passage and an airflow returning passage are defined in the heat-resistant housing such that the two passages are in airtight communication with the detection chamber, wherein the portable odor detector further comprises a pump base which is coupled to the air pump, wherein two connectors are secured on a side of the pump base, wherein one of the connectors is in communication with the air flow sampling passage and the other connector is in communication with the airflow returning passage, wherein the housing in which the battery assembly and the sampling unit are held comprises an opening through which one of the connectors at least partially passes and another opening through which the other connector at least partially passes, wherein by operating the air pump, a test airflow from an object to be tested can be sucked into the detection chamber through the airflow sampling passage and then discharged out through the airflow returning passage, wherein the odor sensor can heat the airflow in the detection chamber so as to decompose gas molecules of the test airflow into charged ions which can be converted to electrical signals, which signals can be transmitted to the circuit board for storage and/or displayed on the display screen as test results, and, wherein the portable odor detector further comprises a piercing unit, the piercing unit includes a sampling needle tube and a returning needle tube, each needle tube is hollow and has a free end which is sharp and closed, the sampling needle tube has an internal passage in airtight communication with the airflow sampling passage, the returning needle tube has an internal passage in airtight communication with the airflow returning passage, and each needle tube is provided with a radial aperture adjacent the sharp free end, which radial aperture is in communication with the internal passage.

2. The portable odor detector according to claim 1, wherein the sampling needle tube is longer than the returning needle tube.

3. The portable odor detector according to claim 1, wherein the odor sensor has a sensor resolution in the range of 2 to 8 μg/L and an operating temperature in the range of 300° C. to 400° C.

4. The portable odor detector according to claim 1, wherein the heat-resistant housing of the sampling unit is made of aluminum alloy.

5. The portable odor detector according to claim 1, wherein the battery assembly comprises a rechargeable battery.

6. The portable odor detector according to claim 1, wherein the display screen is a touch screen which can be used to control the sampling unit.

7. The portable odor detector according to claim 1, wherein the airflow sampling passage is substantially parallel to the airflow returning passage, and the sampling needle tube is substantially parallel to the returning needle tube.

8. A method for operating a portable odor detector according to claim 1, comprising:
   powering on the portable odor detector and activating its odor sensor only;
   activating an air pump of the portable odor detector only after a first standby time;
   connecting an airflow sampling passage of the portable odor detector to a object to be tested, only after a second standby time, to carry out odor detection.

9. The method for operating a portal odor detector according to claim 8, wherein during the odor detection, prior to each odor test, separating the portable odor detector from the object to be tested, activating the air pump of the portable odor detector and waiting for the second standby time.

10. The method for operating a portal odor detector according to claim 8, wherein the first standby time is greater than the second standby time.

* * * * *